(12) United States Patent
Earle et al.

(10) Patent No.: US 10,465,015 B2
(45) Date of Patent: Nov. 5, 2019

(54) LENTINAN EXTRACTION PROCESS FROM MUSHROOMS USING IONIC LIQUID

(71) Applicant: K Hughes & Co., Ltd., Belfast (GB)

(72) Inventors: Martyn Earle, Belfast (GB); Manuela Gilea, Belfast (GB)

(73) Assignee: K Hughes & Co., Ltd., Belfast (GB)

( * ) Notice: Subject to any disclaimer, the term of this patent is extended or adjusted under 35 U.S.C. 154(b) by 55 days.

(21) Appl. No.: 14/387,392

(22) PCT Filed: Mar. 22, 2013

(86) PCT No.: PCT/GB2013/050762
§ 371 (c)(1),
(2) Date: Sep. 23, 2014

(87) PCT Pub. No.: WO2013/140185
PCT Pub. Date: Sep. 26, 2013

(65) Prior Publication Data
US 2015/0099871 A1    Apr. 9, 2015

(30) Foreign Application Priority Data

Mar. 23, 2012 (GB) .................................. 1205179.3

(51) Int. Cl.
C08B 37/00 (2006.01)
A61K 31/716 (2006.01)
C07C 29/74 (2006.01)
C07J 9/00 (2006.01)

(52) U.S. Cl.
CPC ........ *C08B 37/0003* (2013.01); *A61K 31/716* (2013.01); *C07C 29/74* (2013.01); *C07J 9/00* (2013.01); *C08B 37/0024* (2013.01)

(58) Field of Classification Search
CPC ........................ C08B 37/0003; C08B 37/0024
See application file for complete search history.

(56) References Cited

U.S. PATENT DOCUMENTS

2009/0270343 A1* 10/2009 Ales .......................... A23L 1/28
514/54

OTHER PUBLICATIONS

Fort et al., Green Chem., 2007, 9, p. 63-69.*
Takegawa et al., Carb. Polym., 2010, 79, p. 85-90.*
Ventura et al., J. Phys. Chem. B., 2009, 113, p. 9304-9310.*
Tomassen et al., Proceedings of the 7th International Conference on Mushroom Biology and Mushroom Products, Arcachon, France, Oct. 4-7, 2011. vol. 1. Oral presentations 2011 pp. 254-262 ref.24. (Year: 2011).*
Hamuro J Rollinghoff M, Wagner H. Induction of cytotoxic peritoneal exudate cells by T-cell immune adjuvants of the beta (1-3) glucantype lentinan and its analogues Immunology 1980;39:551.
Isoda N, Eguchi Y, Nukaya H, et al., Hepatogastroenterology Mar.-Apr. 2009;56(90):437-41.
Oba K, Kobayashi M, Matsui T, Kodera Y, Sakamoto J. Individual patient based meta-analysis of lentinan for unresectable/recurrent gastric cancer. Anticancer Res. Jul. 2009;29(7):2739-45.
Hazama S, Watanabe S, Ohashi M, et al. Efficacy of orally administered superfine dispersed lentinan (beta-1,3-glucan) for the treatment of advanced colorectal cancer. Anticancer Res. Jul. 2009;29(7):2611-7).
Shimizu K, Watanabe S, Watanabe S, et al. Efficacy of oral administered superfine dispersed lentinan for advanced pancreatic cancer Hepatogastroenterology. Jan.-Feb. 2009;56(89):240-4.
Surenjav U, Zhang L, Xu L, Zhang X, Zeng F. Effects of molecular structure on anti-tumor activities of (1-3)-β-D-glucans from different Lentinus Edodes. Carbohydrate polymers 2006,63,97-104.
Yang B, Jiang Y, Wang R, Zhoa M, Sun J. Ultra-high pressure treatment on polysaccharides and ligins of longan fruit pericarp. Food Chemistry 2009, 112428-431.
Lui J, Peng J, Chi Y, Jiang G. Determination of formaldehyde in shiitake mushroom by ionic liquid-based liquidphase microextraction coupled with liquid chromatography, Ta/anta 2009, 65, 705-709.
4-(2-hydroxyethyl)-1-piperazineethanesulfonic acid (HEPES).
Denaturation and Renaturation of a β-1,6;1,3-Glucan,Lentinan, Associated with Expression of T-cell-mediated Responses Yukiko Y. Maeda, Cancer Research 1988, 48, 671-675.

* cited by examiner

*Primary Examiner* — Jonathan S Lau
(74) *Attorney, Agent, or Firm* — Ryan T. Grace; Advent, LLP (57) ABSTRACT

A method of extracting lentinan from lentinan containing mushrooms comprising the step of contacting the mushrooms with an ionic liquid so as to obtain a lentinan rich ionic liquid solution.

43 Claims, 6 Drawing Sheets

LENTINAN EXTRACTION PROCESS FROM MUSHROOMS USING IONIC LIQUID

The present invention is directed to methods for the extraction of lentinan, and more specifically to methods comprising the use of ionic liquids in the extraction of lentinan, as well as lentinan obtained therefrom.

Anti-cancer and anti-viral properties of polysaccharides found in *Lentinus edodes*, a species of edible mushroom have been utilised for medicinal reasons for over three thousand years.

Polysaccharides such as lentinan have been used to reduce the size of cancerous tumours, though lentinan itself does not display any levels of toxicity to the host nor does it show any specific antitumor activity. It is believed that lentinan creates anti-cancer and anti-viral effects by activating T-cells, natural killer cells and macrophages thereby enhancing a host's natural immune system (see for example Hamuro J, Rollinghoff M, Wagner H. Induction of cytotoxic peritoneal exudate cells by T-cell immune adjuvants of the beta (1→3) glucan-type lentinan and its analogues. *Immunology* 1980; 39:551).

Lentinan has been shown to give positive results for patients with hepatocellular carcinoma (Isoda N, Eguchi Y, Nukaya H, et al., *Hepatogastroenterology*. 2009 March-April; 56(90):437-41), gastric (Oba K, Kobayashi M, Matsui T, Kodera Y, Sakamoto J. Individual patient based meta-analysis of lentinan for unresectable/recurrent gastric cancer. *Anticancer Res*. 2009 July; 29(7):2739-45), colorectal (Hazama S, Watanabe S, Ohashi M, et al. Efficacy of orally administered superfine dispersed lentinan (beta-1,3-glucan) for the treatment of advanced colorectal cancer. *Anticancer Res*. 2009 July; 29(7):2611-7), and pancreatic (Shimizu K, Watanabe S, Watanabe S, et al. Efficacy of oral administered superfine dispersed lentinan for advanced pancreatic cancer. *Hepatogastroenterology*. 2009 January-February; 56(89): 240-4) cancers.

Conformational studies have shown that lentinan is composed of a (1→3)-β-D-glucan having two (1→6)-β-glucaopyranoside branches for every five (1→3)-β-glucopyranoside linear linkages.

Lentinan typically exists as a triple-helical structure, however, when exposed to water/dimethyl sulfoxide (DMSO) mixtures, aqueous NaOH solutions or temperatures of approximately 140° C. or above the conformation of the triple-helix is transformed into single random coils.

It has been shown that the anti-cancer/anti-viral properties of the triple-helix lentinan are significantly diminished or even absent in the single coil structure.

Although the medicinal benefits of lentinan are known, there has proven to be many difficulties in the extraction of lentinan whist retaining the active triple-helical structure.

Known extraction methods can be classified as either solvent extraction or ultrasonic and ultrahigh pressure extraction.

Solvent extraction methods commonly use hot water, an alkali solution or polyethylene glycol.

A crude extract of lentinan can be produced from washing Lentinan edodes with hot water (100° C.). This method can require up to 5 liters of boiling water per kg of fresh fruit bodies wherein the extraction process takes between 8 and 15 hours. After which the suspension is filtered and centrifuged to remove insoluble matter. The crude material is concentrated and subsequently precipitated using ethanol. The precipitate is then re-dissolved in an alkali solution, filtered and neutralised using a dilute acid.

Hot water extractions have been shown to be inefficient, producing low yields of letinan (0.12%). Further the high temperatures used to extract the lentinan can denature the conformational structure to the single random coil structure.

Alkali extraction methods have also been proposed as an alternative in seeking to improve the yield of lentinan extracted. This method requires the use of, for example, a 1.25M NaOH/0.05% $NaBH_4$ solution to extract lentinan from the fresh or dried fruit bodies. The extraction method alleges that it is more effective, producing a yield of up to 5% isolated lentinan. However, the alkali nature of the solvent irreversibly denatures the conformational structure of lentinan producing an inactive compound.

Alternatively, lentinan can be extracted through ultrasonic and ultrahigh pressure extraction methods.

Ultrasonic wave extraction firstly soaks *Lentinus edodes* powder in distilled water, after which the solution is treated ultrasonically for up to 40 minutes at powers of approximately 90 W. Lentinan is then extracted using a hot water (up to 100° C.) extraction method or using a $NaOH/NaBH_4$ extraction. The water is then removed and excess amounts of anhydrous ethanol are added. The solution is subsequently cooled and the precipitate collected.

As briefly noted above, studies have shown that the anti-tumor activity of lentinan is related to both the conformational structure and the molecular weight of the compound, wherein higher molecular weights have been shown to exhibit higher levels of anti-tumor activity (Surenjav U, Zhang L, Xu L, Zhang X, Zeng F. Effects of molecular structure on anti-tumor activities of (1→3)-β-D-glucans from different *Lentinus edodes*. *Carbohydrate polymers* 2006, 63, 97-104). Although ultrasonic extraction techniques are able to extract lentinan without altering the conformation, the compounds produced exhibit low molecular weight and have been shown to display lower antitumor activities compared to lentinan extracted using NaOH/NaBH$_4$ alone.

Ultrahigh pressures (approximately 400 MPa) can be used to accelerate the speed of the extraction without the use of high temperatures or alkali solutions.

Although the time required to extract lentinan is drastically reduced (2 hours) with the use of ultra-high pressure extraction, the structure and yield of lentinan can be effected through use of this method. Recent research (Yang B, Jiang Y, Wang R, Zhoa M, Sun J. Ultra-high pressure treatment on polysaccharides and ligins of longan fruit pericarp. *Food Chemistry* 2009, 112 428-431) has demonstrated that the pressures required during extraction (up to 500 MPa) can lead to the dissociation or denaturation of some macromolecules. Further it has been suggested that the structural arrangement of water soluble polysaccharides, such as lentinan, could be altered during the extraction process. This research has also demonstrated a negative correlation with regard to the amount of lentinan extracted and the pressure under which the extraction occurs, wherein the highest yields are found at ambient pressure (18.3±0.8 mg/g) and the lowest yields produced at 500 MPa (6.4±0.6 mg/g).

Further, these methods of extraction are likely to be more costly, also the ultrasonic method clearly comprises additional extraction steps wherein hot water extraction is used.

Known methods for extracting lentinan, such as hot water extraction, have been shown to be highly inefficient, wherein the extraction process produced an approximate yield of 0.15%. Efforts to increase the amount of lentinan extracted from lentinan rich mushrooms have relied on harsher extraction conditions, such as strong alkali solutions, high pressure and ultrasonification. These harsher extraction conditions have been shown to, at best, fracture the lentinan extracted and thereby reducing the molecular weight of the compound or at worst, completely denaturing the lentinan structure causing a conformational change from the triple helix to the single coil structure. The anti-cancer activity of lentinan has been inextricably linked to the complicated three-dimensional triple helical structure wherein the extent of the anti-tumour activity is linked to the molecular weight of the compound extracted.

In the known prior art processes it is believed that the triple helix-structure is transformed into the inactive single coil structure due to the use of denaturants such as dimethyl sulfoxide (DMSO), urea and sodium hydroxide (NaOH). The denaturants work by disrupting the hydrogen bonding within the triple-helical structure. It has been reported that the glucoside bond to alkali is relatively strong and the denaturation of the structure occurs with the formation of D-glucometasaccharinates from a peeling process created by the reduction of the end unit. The degree of peeling can be measured through the specific rotation value ($[\alpha]_D$) of the structure.

By way of example, pure lentinan in the triple-helix form displays a specific rotation value of 25° in water. Upon addition of urea (6 M) this value is decreased to 2°.

Further, the use of DMSO (100%) reduces the $[\alpha]_D$ value for lentinan to −16°. Whilst dialysis has shown that this value can be increased to 17°, i.e. by producing a triple-helix-like structure through recombination, the conformation produced is not identical to the natural triple-helix structure. Given that many studies have shown the antitumor activity of lentinan is linked to the specific conformational structure, such a difference is thought to be an indication of reduced activity.

In another example, the addition of 1% NaOH to lentinan resulted in a specific rotation value of −2°. After treatment with dialysis this value increased to 17 to 20°. Whilst some anti-tumor activity has been observed after renaturation in cases where low levels (1%) of NaOH had been used, the use of NaOH in concentrations above 2% NaOH results in a significant loss of bioactivities, even after attempts to recover the triple-helix conformation.

Accordingly, there is a need in the art to find an alternative extraction method, especially one which seeks to alleviate one or more of the issues discussed above.

Ionic liquids are a class of compounds which have been the subject of intense research over the past few decades. The term "ionic liquid" as used herein refers to a liquid that is capable of being produced by melting a solid, and when so produced consists solely of its ions.

A feature of ionic liquids is that they have particularly low (essentially zero) vapour pressures. Many organic ionic liquids have low melting points, for example, less than 100° C., particularly less than 80° C., and around room temperature, e.g. 15 to 30° C., and some have melting points well below 0° C.

An ionic liquid may be formed from a homogeneous substance comprising one species of cation and one species of anion, or it can be composed of more than one species of cation and/or anion. Thus, an ionic liquid may be composed of more than one species of cation and one species of anion. An ionic liquid may further be composed of one species of cation and more than one species of anion.

The present inventors have surprisingly found that ionic liquids may be used to extract lentinian from mushrooms containing natural lentinan.

Whilst ionic liquids have been disclosed with respect to shiitake mushrooms, it is solely in the context of detecting formaldehyde (Lui J, Peng J, Chi Y, Jiang G. Determination of formaldehyde in shiitake mushroom by ionic liquid-based liquid-phase microextraction coupled with liquid chromatography, *Talanta* 2009, 65, 705-709). This research discloses that the detection of formaldehyde is based on it's reaction with 2,4-dinitrophenylhydrazine (DNPH) to form the corresponding hydrozone (DNPHo). The subsequent hydrozone is extracted using a liquid-liquid extraction, solid-phase extraction or solid-phase microextraction. A drop of ionic liquid from a microsyringe, such as 1-octyl-3-methylimiazolium hexafluorophosphate ([C$_8$MIM][PF$_6$]), is used as an extraction fluid, wherein the DNPH compound, once extracted, can be analysed through HPLC. At no time does the ionic liquid come into contact with the crude mushroom bodies.

The research does not disclose a method of extracting formaldehyde from a shiitake mushroom using an ionic liquid, but teaches the use of leaching the formaldehyde from the mushroom using water wherein the volume of formaldehyde extracted is detected through a reaction with 2,4-dinitrophenylhydrazine. Ionic liquids are used only to extract the corresponding hydrazone compound.

This method does not teach the use of ionic liquids for extracting organic molecules from shiitake mushrooms. Further the research disclosed teaches an extraction method of a simple aldehyde structure as opposed to the present invention which teaches the extraction of a complex biomolecule wherein the conformation of the compound must be unaffected by the extraction process.

According to an aspect of the present invention there is provided a method of extracting lentinan from lentinan containing mushrooms comprising the step of contacting the mushrooms with an ionic liquid so as to obtain a lentinan rich ionic liquid solution.

Suitable lentinan containing mushrooms include *Collybia shiitake, Armillaria edodes, Agaricus russaticeps, Lepiota shiitake, Lentinus tonkinensis, Mastaleucomyces edodes, Pleurotus russaticeps, Cortinellus shiitake, Tricholoma shiitake, Cortinellus edodes* and *Lentinula edodes*. These mushrooms are more commonly referred to as black forest mushroom, black oak mushroom, golden oak mushroom, snake butter, pasania mushroom, oakwood mushroom, japanese forest mushroom

Preferably, the ionic liquid is a hydrophilic ionic liquid.

For the avoidance of any doubt, a person of skill in the art would understand that the term 'hydrophilic ionic liquid' refers to an ionic liquid which is miscible with water in any ratio to form a homogeneous liquid under standard conditions, i.e. 20° C. and 101.325 kPa. In other words, the mixture does not have any miscibility gap over the entire composition range from >0% of water (or <100% ionic liquid) to <100% of water (or >0% of IL).

In an embodiment of the present invention, the ionic liquid comprises a hydrophilic cation.

In accordance with the present invention, the cation may be selected from ammonium, azaannulenium, azathiazolium, benzofuranium, borolium, diazabicyclodecenium, diazabicyclononenium, diazabicycloundecenium, dithiazolium, furanium, imidazolium, indolinium, indolium, morpholinium, oxaborolium, oxaphospholium, oxazinium, oxazolium, iso-oxazolium, oxothiazolium, pentazolium, phospholium, phosphonium phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenozolium, tetrazolium, iso-thiadiazolium, thiazinium, thiazolium, thiophenium, triazadecenium, triazolium and iso-triazolium.

In one aspect, the cation is preferably selected from:

-continued and wherein: $R^a$, $R^b$, $R^c$, $R^e$, $R^f$ and $R^g$ are each independently selected from hydrogen, a $C_1$ to $C_{10}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —(CH$_2$)$_q$— wherein q is from 3 to 6; and wherein said alkyl, cycloalkyl or aryl groups or said methylene chain are unsubstituted or may be substituted by one to three groups selected from: $C_1$ to $C_6$ alkoxy, $C_3$ to $C_8$ cycloalkyl, $C_6$ to $C_{10}$ aryl, $C_7$ to $C_{10}$ alkaryl, $C_7$ to $C_{10}$ aralkyl, —O, —OH, —NO$_2$, —CO$_{-2}$ $R^x$, —OC(O)$R^x$, —C(O)$R^x$, —NR$^x$C(O)NR$^y$R$^z$, —NR$^x$C(O)OR$^y$, —OC(O)NR$^y$R$^z$, —C(O)NR$^y$R$^z$, —NR$^y$R$^z$, or a heterocyclic group, wherein $R^x$, $R^y$ and $R^z$ are independently selected from hydrogen or $C_1$ to $C_6$ alkyl.

Preferably, $R^a$, $R^b$, $R^c$, $R^d$, $R^e$, $R^f$ and $R^g$ are each independently selected from hydrogen, a $C_1$ to $C_{10}$, straight chain or branched alkyl, optionally substituted by —O—.

More preferably, $R^a$ and $R^g$ are each independently selected from $C_1$ to $C_8$, linear or branched, alkyl. For example, $R^a$ and $R^g$ may each independently be selected from methyl, ethyl, n-propyl, n-butyl, n-pentyl, n-hexyl, n-heptyl and n-octyl.

In one embodiment, wherein $R^b$, $R^c$, $R^d$, $R^e$ and $R^f$, where present, are each hydrogen or are each are each independently selected from $C_1$ to $C_8$, linear or branched, alkyl. For example, $R^b$, $R^c$, $R^d$, $R^e$ and $R^f$, where present, are each hydrogen or are each are each independently selected from methyl, ethyl, n-propyl, n-butyl, n-pentyl, n-hexyl, n-heptyl and n-octyl. In a further example, $R^b$, $R^c$, $R^d$, $R^e$ and $R^f$, where present, are each hydrogen.

In a preferred embodiment, the cation is selected from:

wherein: $R^a$, $R^b$, $R^c$, $R^d$, $R^e$, $R^f$, and $R^g$ are as defined above.

More preferably, the cation is selected from:

wherein: $R^a$ and $R^g$ are as defined above, and $R^h$ represents hydrogen or a methyl group.

Preferred cations for use in the present invention may be selected from:

Preferred cations for use in the present invention may also be selected from:

$[N(R^a)(R^b)(R^c)(R^d)]^+$ wherein: $R^a$, $R^b$, $R^c$ and $R^d$ are each independently selected from hydrogen, a $C_1$ to $C_{10}$, straight chain or branched alkyl group, a $C_3$ to $C_8$ cycloalkyl group, or a $C_6$ to $C_{10}$ aryl group; and wherein said alkyl, cycloalkyl or aryl groups or said methylene chain are unsubstituted or may be substituted by one to three groups selected one to three groups selected from: $C_1$ to $C_6$ alkoxy, $C_3$ to $C_8$ cycloalkyl, $C_6$ to $C_{10}$ aryl, $C_7$ to $C_{10}$ alkaryl, $C_7$ to $C_{10}$ aralkyl, —O, —OH, —NO$_2$, —CO$_2$R$^x$, —OC(O)R$^x$, —C(O)R$^x$, —NR$^x$C(O)NR$^y$R$^z$, —NR$^x$C(O)OR$^y$, —OC(O)NR$^y$R$^z$, —C(O)NR$^y$R$^z$, —NR$^y$R$^z$, or a heterocyclic group, wherein R$^x$, R$^y$ and R$^z$ are independently selected from hydrogen or $C_1$ to $C_6$ alkyl, and wherein one of $R^a$, $R^b$, $R^c$ and $R^d$ may also be hydrogen.

Preferably $R^a$, $R^b$, $R^c$ and $R^d$ are each independently selected from hydrogen, a $C_1$ to $C_{10}$, straight chain or branched alkyl, optionally substituted with by —O— or —OH, and wherein one of $R^a$, $R^b$, $R^c$ and $R^d$ may also be hydrogen.

More preferably $R^a$, $R^b$, $R^c$ and $R^d$ are independently selected from methyl, ethyl, n-propyl, n-butyl, n-pentyl, n-hexyl, n-heptyl, and n-octyl, and optionally substituted by —O— or —OH.

Most preferably two or more, and most preferably three or more, of $R^a$, $R^b$, $R^c$ and $R^d$ are independently selected from methyl, ethyl, propyl and butyl.

In one preferred embodiment $R^b$, $R^c$, $R^d$ are each the same alkyl group selected from methyl, ethyl n-butyl, and n-octyl, and $R^a$ is selected from hydrogen, methyl, n-butyl, n-propyl, n-pentyl, n-hexyl, n-hepty n-octyl, n-tetradecyl, 2-hydroxyethyl, or 4-hydroxy-n-butyl.

In a preferred embodiment the preferred cations are selected from:

In accordance with the present invention the ionic liquid may comprise a hydrophilic anion.

In one embodiment the anion is selected from inorganic anions, sulfonate anions, fluorinated anions, sulphate anions, carboxylate anions, carbonate anions and metal anions.

Preferred hydrophilic anions include inorganic anions selected from [F]$^-$, [Cl]$^-$, [Br]$^-$, [I]$^-$, [NO$_3$]$^-$, [BF$_4$], [HSO$_4$]$^-$, and [SO$_4$]$^{2-}$; fluorinated anions selected from [CF$_3$CO$_2$]$^-$, [CF$_3$SO$_3$]$^-$ and [(C$_2$F$_5$)$_3$PF$_3$]$^-$; sulfonate anions selected from [CH$_3$SO$_3$]$^-$, [C$_2$H$_5$SO$_3$]$^-$ and [bis(2-ethylhexyl)-sulfosuccinate]$^-$ (also referred to as [AOT]$^-$); carboxylate anions selected from [CH$_3$CO$_2$]$^-$ and [CH$_3$CH$_2$CO$_2$]$^-$; the carbonate anion [HCO$_3$]$^-$; and sulphate anions selected from [CH$_3$OSO$_3$]$^-$, [C$_2$H$_5$OSO$_3$]$^-$, [C$_8$H$_{17}$OSO$_3$]$^-$ and [H$_3$C(OCH$_2$CH$_2$)$_n$OSO$_3$]$^-$.

More preferably, the anion may be selected from [F]$^-$, [Cl]$^-$, [Br]$^-$, [CH$_3$CO$_2$]$^-$ and [CH$_3$CH$_2$CO$_2$]$^-$.

In one embodiment the ionic liquid may comprise of a cation and multiple anions, alternatively the ionic liquid may comprise an anion and multiple cations. In another embodiment of the present invention the ionic liquid used may comprise mixtures of multiple anions and cations.

The present invention is not limited to ionic liquids comprising anions and cations having only a single charge. Thus, the formula [Cat]$^+$[X]$^-$ is intended to encompass ionic liquids comprising, for example, doubly, triply and quadruply charged anions and/or cations. The relative stoichiometric amounts of [Cat]$^+$ and [X]$^-$ in the ionic liquid are therefore not fixed, but can be varied to take account of cations and anions with multiple charges. For example, the formula [Cat]$^+$[X]$^-$ should be understood to include ionic liquids having the formulae [Cat]$^+_2$[X]$^{2-}$, [Cat]$^{2+}$[X]$^-_2$, [Cat]$^{2+}$[X]$^{2-}$, [Cat]$^+_3$[X]$^{3-}$, [Cat]$^{3+}$[X]$^-_3$ and so on.

In one embodiment the ionic liquid may further comprise a solvent. The solvent may be selected from suitable solvents known in the art, for example, water, acetate, lactates, dicyanamides, aqueous phosphates and urea.

In a preferred embodiment the ionic liquid may further comprise water.

Where the viscosity of the chosen ionic liquid is high, a solvent, such as a water-in-ionic liquid solution, may be used to reduce the viscosity of the extraction solution so as to aid contacting the lentinan rich mushroom with the ionic liquid. The extraction solution may also be used to further extract lentinan from the lentinan rich mushroom, for example, water may be used as an extraction solution.

In a preferred embodiment, the extraction solution contains no solvent or where required a minimal amount of solvent is used, as it is believed that the molecular weight of lentinan extracted may be affected by the solvents, for example using cold (not boiling) water results in a reduction of molecular weight. This may effect the anti-cancer activity of the lentinan extracted.

The solvent-in-ionic liquid solutions used in the present invention may comprise an ionic liquid to solvent ratio from 99:1 to 50:50. Preferably the ionic liquid to solvent ratio is from 99:1 to 60:40, more preferably the ionic liquid to solvent ratio is from 99:1 to 75:25.

Where urea is used as a solvent, the ratio of ionic liquid to solvent may be in the range of 20:80 to 50:50, more preferably 30:70 to 40:60. By way of example, the ionic liquid to urea ratio may be 1:2.

As discussed above, the anti-cancer activity of the lentinan extracted has been linked to the conformational structure of the compound wherein the triple-helical structure has been shown to exhibit anti-cancer activity however the single coiled structure shows activity which is significantly diminished or even absent. On this basis lentinan must be partitioned from the lentinan rich mushroom without substantially altering the conformational structure of the compound.

It is believed that high temperatures, for example temperatures above 100° C., may dissociate and/or denature lentinan, thereby producing the inactive single coiled structure.

Accordingly, in a preferred embodiment, the contacting step is undertaken at temperatures less than 100° C., preferably at a temperature of 15 to 90° C., more preferably at a temperature of 25 to 80° C. For example, temperatures of 40 to 80° C., including temperatures of 60 to 80° C., are also contemplated.

Lentinan can be extracted from mushrooms in both the wet and dried form. In this way, it will be understood that the ionic liquids may be used for both liquid-liquid and solid-liquid extractions.

Wet mushrooms are considered to comprise fresh mushrooms. The mushrooms are preferably masticated prior to contact with the ionic liquid. Such mushrooms preferably have not been dried.

Dried mushrooms are considered to comprise fresh mushrooms which have been subsequently dehydrated by storing the fruit bodies in an oven, freeze-drying, spray-drying, exposing the fruit bodies to a belt filter press or any other drying method known in the art. During the drying process, the mushrooms may be exposed to temperatures up to 100° C. for time periods of up to 48 hours. It is noted that longer drying times may be used should a person skilled in the art consider the mushrooms to still retain water after this time period.

The reference to dried mushrooms as used herein, is also intended to include lentinan which has been obtained from other known extraction processes. By way of example, it is possible to obtain commercially extracted lentinan in dried form. Such extracted lentinan is suitable for use in the methods of the present invention.

The dried mushrooms may be in granular form when used in accordance with the present invention.

In accordance with the present invention, lentinan can be extracted from lentinan containing mushrooms in either the wet or dry form wherein the extraction step comprises contacting the mushroom with an ionic liquid.

During the extraction process, the contact time may be between 10 minutes and 48 hours, preferably between 20 minutes and 24 hours, for example between 30 minutes and 4 hours. However it is noted that longer contact times may be used after an initial time period.

In one embodiment the extraction step, comprising contacting the lentinan containing mushroom with an ionic liquid, may be repeated to maximise the amount of lentinan removed from the lentinan containing mushrooms, wherein the contacting step may be repeated, for example, up to four times. It will be appreciated that repeating the step two or three times may also be suitable.

Further, it will also be appreciated that should a person skilled in the art observe that the supernatant still contains lentinan extract from one of the further contacting steps, for example a fourth separation, additional contacting steps can be performed until no further lentinan is observed in the supernatant.

The lentinan contained within the lentinan containing mushroom is transferred into the ionic liquid solution during the contacting period. In one embodiment the lentinan rich ionic liquid may be filtered to separate the lentinan rich ionic liquid from any remaining fruit body.

As used herein, the term filtered is understood to mean any technique which can be used to separate the lentinan rich ionic liquid from the remaining mushroom fruit body. In accordance with the present invention the filtering step may comprise the use of a filtration system, a centrifuge, ultra-high pressure separation, or any method of separating solids and liquids known in the art.

Filtration and centrifuging are preferred in the context of the present invention.

Where the viscosity of the chosen ionic liquid is high enough so as to prevent ease of filtration, water may be added so as to reduce the overall viscosity.

Where water is present, it can be removed from the water/ionic liquid mixture through drying at temperatures of up to 100° C., preferably at temperatures of less than 80° C. Suitable methods include chromatographic methods, distillation methods and any other suitable liquid/liquid separation methods known in the art.

As noted above, the drying step is undertaken at a temperature of less than 100° C., preferably less than 80° C., as it is believed (see comments above) that high temperatures, for example temperatures above 100° C., may dissociate and/or denature lentinan, and thereby produce the inactive single coiled structure.

In accordance with the present invention, the lentinan may be separated from the lentinan rich ionic liquid solution by precipitating the lentinan from the lentinan rich ionic liquid. The precipitation may be induced through the addition of a precipitating agent. Preferably the precipitating agent is selected from an alcohol. Preferred alcohols include methanol, ethanol, iso-propanol or combinations thereof. Most preferably the precipitating agent is ethanol or industrial methylated spirits (IMS).

As used herein, the term IMS is understood to be an ethanol solvent containing an additive, wherein the additive can be selected from methanol, isopropyl alcohol, methyl ethyl ketone, methyl isobutyl ketone. Preferably, the IMS is an ethanol solvent containing up to 10% methanol as an additive.

In a preferred embodiment the precipitating agent is sequentially added. It has been found that the volume of precipitating agent added controls the order of precipitation of compounds which are precipitated from the lentinan rich ionic liquid solution. In particular, it has been found that lentinan is the first precipitate formed when sequentially adding the precipitating agent.

The present invention may further comprise the step of washing and drying the precipitated lentinan in order to further purify the lentinan product.

The lentinan extract may be washed with any suitable polar solvent with a boiling point at or below 100° C., wherein the polar solvent may be chosen from water, methanol, ethanol, iso-propanol, acetic acid, acetone or industrial methylated spirits (IMS) or combinations thereof. Most preferably the washing step is performed using an IMS solvent (such as a 50:50 mixture with water) or a water/ethanol mixture (such as a 50:50 mixture).

The lentinan precipitate may be separated from the solvent by the use of a filtration system, a centrifuge, ultra-high pressure separation, or any method of separating solids and liquids known in the art.

The present invention may further comprise the step of subjecting the extracted lentinan to a dialysis step in order to increase the proportion of triple-helix conformation within the lentinan extract.

In one embodiment the dialysis step may comprise a dialysis step against water.

The membrane used for the dialysis may comprise natural cellulose, regenerated cellulose, cellulose ester or polyvinylidene fluoride.

Suitable membranes include those having a molecular weight cut-off specification of between 1,000 and 50,000 Da. More preferably the membrane pore size is between 5,000 and 40,000 Da. Most preferably the membrane pore size is in the range of 10,000 to 30,000.

The dialysis step may also comprise the use of a buffer solution. The buffer solution may be selected from water, a phosphate based buffer, a tris buffer saline, an amino acid based buffer, a zwitterionic buffer such as 4-(2-hydroxyethyl)-1-piperazineethanesulfonic acid (HEPES) and an alkaline buffer.

The separation may be performed at temperatures in the range of 0° C. to 100° C. It will be appreciated that it is preferable to keep the temperature below 100° C. so as to avoid loss of the triple-helix conformation. Temperatures of less than 80° C. are also preferred.

In another embodiment the dialysis step may be carried out for a period of up to ten days.

Such a suitable process is disclosed in, "Denaturation and Renaturation of a β-1,6,1,3-Glucan, Lentinan, Associated with Expression of T-cell-mediated Responses". Yukiko Y. Maeda, Cancer Research 1988, 48, 671-675, where dialysis against water is disclosed.

The precipitated lentinan may then be dried at a temperature of less than 100° C., preferably less than 80° C., as it is believed that high temperatures, for example temperatures above 100° C., denature lentinan and thereby produce the inactive single coiled structure.

In one embodiment of the present invention the precipitated lentinan may be freeze-dried and/or spray-dried. The freeze-drying step may comprise the use of solvents such and dry-ice and methanol or liquid nitrogen for use in dehydrating the lentinan extract. The spray-drying step may comprise the use of a hot drying medium such as air or nitrogen.

The dried extract produced in accordance with the present invention may be ground into a powder using known means.

The method of the present invention may further comprise the step of pre-treating the lentinan containing mushrooms.

In one embodiment the pre-treatment steps may comprise treating the lentinan containing mushrooms with a solvent so as to at least partially remove wax and/or steroids contained therein.

The wax and/or steroid extraction can comprise washing the lentinan rich mushrooms with up to 5 liters of extraction solvent per kg of lentinan rich mushroom.

In a preferred embodiment the wax and/or steroids contained within the mushrooms are removed by an extraction step comprising washing the lentinan containing mushrooms with an organic solvent. Preferably the organic solvent comprises an ether, an ester, an ether/hexane solution, an ester/hexane solution or an alcohol/hexane solution. In a more preferred embodiment the organic solvent may be selected from diethyl ether, tetrahydrofuran, dioxane, methyl acetate, ethyl acetate, isopropyl acetate, isobutyl acetate, an ethyl acetate/hexane solution and an alcohol/hexane solution. The alcohol/hexane solution may comprise an alcohol selected from methanol, ethanol propanol, isopropanol or butanol. Most preferably the organic solvent is ethyl acetate.

In accordance with the present invention the wax and/or steroid extraction step comprises contacting the mushrooms with a solvent at temperatures of less than 100° C., preferably at a temperature of 15 to 90° C., more preferably at a temperature of 25 to 80° C., still more preferably at a temperature of 40 to 80° C., most preferably at a temperature of 60 to 80° C.

The wax and/or steroid removal step does not exceed temperatures of 100° C. as it is believed that high temperatures, for example temperatures above 100° C., denature lentinan and thereby producing the inactive single coiled structure.

In one embodiment the wax and/or steroid extraction step comprises contacting the lentinan containing mushrooms and an organic solvent for a contact time of, for example, between 10 minutes and 48 hours, preferably between 20 minutes and 24 hours, more preferably between 30 minutes and 4 hours. However, it will be noted that longer contact times may be used where a person skilled in the art considers that further wax and/or steroids may be extracted after this time period.

It will be appreciated by those of skill in the art that the wax and/or steroid extraction step may be repeated to maximise the amount of wax and/or steroids removed from the mushrooms. The wax and/or steroid extraction step may be repeated, for example, up to four times. Two and three times may also be suitable. Further, it will be appreciated that should a person skilled in the art observe that the supernatant still contains wax and/or steroid compounds from the, for example fourth extraction, additional separation steps can be performed until no further wax and/or steroids are observed.

The steroids removed from the extraction step may comprise ergosterol, which is shown in the formula below:

The ergosterol can be isolated using known separation means and processes.

The compound is a precursor for the formation of vitamin $D_2$, wherein ergosterol is converted into viosterol by interaction with UV light. Viosterol can then be converted in to ergocalciferol through reacting viosterol with methanol, pyridine and 3,5-dinitrobenzoyl chloride solution and further reacting the product with sodium hydroxide and ethanol. Ergocalciferol is more commonly referred to as vitamin $D_2$. Accordingly, it will be appreciated that the compound has commercial value and therefore there is a benefit in its isolation.

In accordance with the present invention, the pre-treatment steps may comprise treating the lentinan containing mushrooms with a solvent so as to at least partially remove sugars contained within the mushrooms. The sugar extraction can comprise washing the lentinan rich mushrooms with up to 5 liters of extraction solvent per kg of lentinan rich mushrooms.

In a preferred embodiment the sugar contained within the mushrooms is removed by an extraction step comprising washing the lentinan containing mushrooms with an organic solvent.

Preferably, the organic solvent comprises an alcohol. In a more preferred embodiment the organic solvent may be selected from methanol, ethanol, iso-propanol or IMS (such as defined above). Most preferably the organic solvent is ethanol. It will be appreciated that a alcohol/hexane solution may also be used.

In accordance with the present invention the sugar extraction step from the lentinan rich mushrooms comprises contacting the mushrooms with an alcohol at temperatures less than 100° C., preferably at a temperature of 15 to 90° C., more preferably at a temperature of 25 to 80° C., still more preferably at a temperature of 40 to 80° C., most preferably at a temperature of 60 to 80° C.

The sugar removal step does not exceed temperatures of 100° C. as it is believed that high temperatures, for example temperatures above 100° C., denature lentinan and thereby producing the inactive single coiled structure.

In one embodiment the sugar extraction step comprises contacting the lentinan containing mushrooms and organic solvent, wherein the contact time may be between 10 minutes and 48 hours, preferably between 20 minutes and 24 hours, more preferably between 30 minutes and 4 hours. However it is noted that longer contact times may be used if a person skilled in the art considers further sugar compounds may be extracted after this time period.

In another embodiment the extraction step comprises contacting the lentinan rich mushroom with an alcohol wherein the extraction step may be repeated to maximise the amount of sugar removed from the mushrooms. The sugar extraction step may be repeated, for example, up to four times. It will be understood that two or three times may also be suitable. It will be appreciated that should a person skilled in the art observe that the supernatant still contains sugar compounds from the, for example fourth extraction, additional separation steps can be performed until no further sugars are observed.

The sugars removed from the extraction step can comprise mannitol as shown in the formula below:

The mannitol extracted may be isolated using known processes. It may be used as an osmotic diuretic wherein mannitol acts within the kidneys to cause excess body water to be removed from the blood.

In this way, it will be appreciated that there is commercial value in being able to obtain the substance as a by-product in the extraction of lentinan.

In accordance to the present invention the order in which the pre-treatment steps, for example, of extracting waxes and/or steroids from the lentinan containing mushrooms and/or the pre-treatment step of removing the sugars from the lentinan rich mushroom are performed is inconsequential.

In a preferred embodiment both of the aforementioned pre-treatment steps are used.

The pre-treatment steps may further comprise the step of washing and/or filtering the lentinan containing mushrooms obtained from the pre-treatment steps.

The lentinan containing mushrooms may be washed using any suitable polar solvent with a boiling point at or below 100° C. Suitable polar solvents may be selected from water, methanol, ethanol, acetic acid, acetone or industrial methylated spirits (IMS), or combinations thereof. Most preferably the washing step is performed using water. Also suitable are mixtures of IMS with water or ethanol with water, such as 50:50 mixtures.

The lentinan containing mushrooms may be separated from the solvent by the use of a filtration system, a centrifuge, ultra-high pressure separation, or any method of separating solids and liquids known in the art. It is preferred to use temperatures of less than 100° C., preferably less than 80° C.

The lentinan rich precipitate may subsequently be dried by the application of heat (up to 100° C.—see suitable temperatures above), the use of a freeze-drying method or any other drying method known in the art.

It will be appreciated that the process of the present invention may be used with other known fortification processes. By way of example, the lentinan obtained from the process of the present invention may be subjected to further purification such as counter-current chromatography, preferably, counter-current chromatography using an ionic liquid solvent system.

In one embodiment, a counter-current chromatography process may be used to purify lentinan extracted from mushrooms in either the wet or dry form, such as that obtained by the processes of the present inventions.

It will also be appreciated that counter-current chromatography may be used to purify lentinan extracted using other known processes.

Such counter-current chromatography processes may be used before or after washing of the lentinan extracts with ionic liquid solutions, such as described above.

In addition, such counter-current chromatography processes may be used before or after washing of the lentinan extracts with polar solvents, such as described above.

Preferably, the counter-current chromatography purified lentinan is washed using a polar solvent, such as described above, after processing.

Suitable counter-current chromatography processes include those such as described in PCT/GB2013/050372.

The method of the present invention provides a cost effective method for extracting lentinan, by use of ionic liquids. In fact, the process of the present invention can be operated as a one-step process unlike those of the prior art.

A further benefit is that the process of the present invention is able to obtain lentinan in relatively high yields—up to 0.5% from wet mushrooms and up to 5% from dried mushrooms.

Yet a further benefit of the process of the present invention is the avoidance of a necessity to use high temperatures which causes the conformational change from the active triple helix conformation to the inactive single strands.

Still a further benefit of the process of the present invention is the avoidance of the use alkaline solvents which causes the conformational change from the active triple helix conformation to the inactive single strands.

Yet a further benefit of the process of the present invention is that it may be operated without the addition of a catalyst.

It will also be appreciated that the ionic liquids used in the methods of the present invention may be recycled using known methods. This is a clear cost benefit, and simplification when compared to known processes.

The present invention will now be described by way of example and with reference to the accompanying figures in which.

GENERAL PROCEDURE FOR LENTINAN FROM DRIED SHITAKE MUSHROOM GRANULES

Example 1

5 Kg of Shitake mushrooms were dried and ground up to form small granules. This mushroom dry matter was purified to lentinan in a 3 step process, wherein fatty acids and other oils are first removed using ethyl ethanoate, followed by the removal of mono-saccharides using ethanol and finally a lentinan extraction using an ionic liquid.

The extraction involved heating the mushroom granules (250 g) with ethyl ethanoate for 4 to 6 hours under reflux, followed by filtration of the mushroom powder. The extraction was carried out twice with ethyl ethanoate and twice with boiling industrial methylated spirits (IMS).

The ethyl ethanoate extracts contained fatty acid derived compounds and other oils such as steroids, for example ergosterol. The ethanol extract removed mono-saccharides such as mannitol.

Ergosterol was easily isolated in pure form by suspending the ethyl ethanoate extract in water/hexane leading to the precipitation of ergosterol.

The ethyl ethanoate and IMS solvents were recovered on a rotary evaporator and reused. It will be appreciated that such a step saves on overall solvent usage and reduces the cost of the overall process.

The resulting brown granules were then extracted with ionic liquid (1000 g), using [C$_4$mim]Cl, for 4 to 48 hours at 70 to 90° C. The ionic liquid extract was mixed with cold water (~10 to 30 wt %) and vacuum filtered through a polypropylene filter. Centrifuging at 4200 rpm for 10 to 15 minutes can also be used.

The supernatant was evaporated under vacuum to remove water (80° C. maximum temperature) then mixed gradually with an equal volume of IMS. The precipitate that formed was isolated by centrifugation (4200 rpm). The resulting solution was mixed with 3 volumes of IMS and the resultant precipitate was isolated using a centrifuge under the same conditions.

The precipitate obtained was washed with IMS until a clear supernatant was observed. The grey-brown precipitate obtained contained lentinan, and was subsequently freeze-dried to a light brown powder (approximately 15 g), with a glycans type polysaccharide content of 10 to 70%, by gel HPLC. This is referred to as crude lentinan.

The solid cake that resulted after the first centrifugation from ionic liquid was re-extracted with ionic liquid under similar conditions and was subject to the same precipitation procedure using IMS, to give a second sample of crude lentinan. The amount of crude lentinan was considerably reduced.

Figure 1:
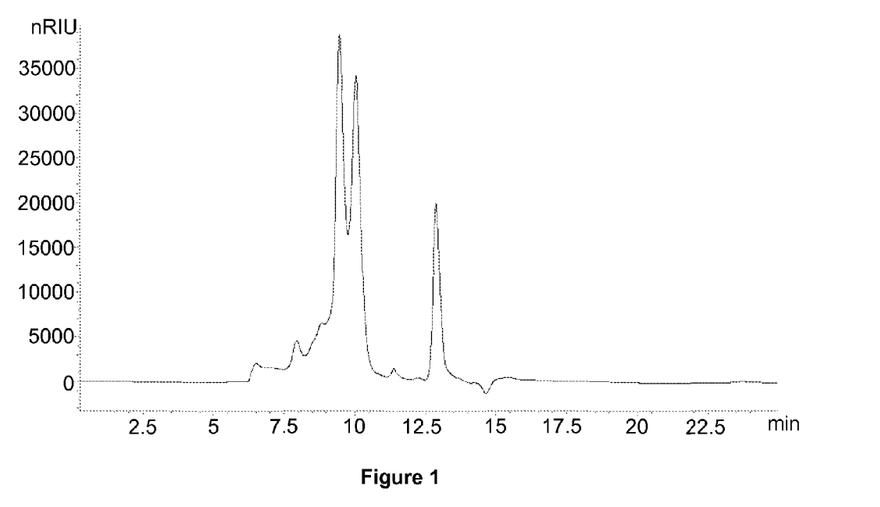
FIG. 1 is a gel-HPLC analysis of lentinan extracted from mushrooms using [C$_4$mim]Cl.

The FIG. 1 chromatogram shows three peaks at approximately 9.5, 10 and 13 minutes corresponding to the triple-helix conformation, the random coil conformation and mono-saccharides respectively. The chromatogram demonstrates that a large portion of the lentinan extracted is maintained in the triple helix structure. The ratio of triple helix to random coil conformation is approximately 60:40.

Figure 2:
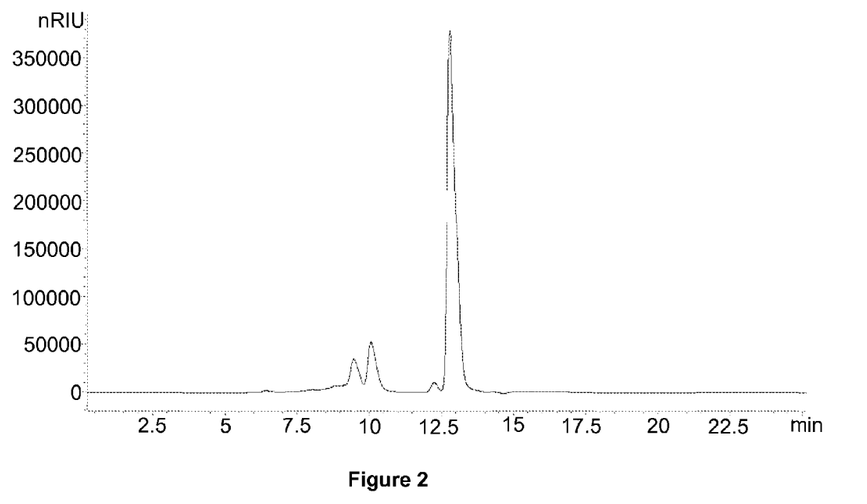
FIG. 2 is a gel-HPLC analysis of the lentinan extraction shown in FIG. 1, wherein the extract has been maintained at 100° C. for six days.

FIG. 2 demonstrates that effect of heating the extract to 100° C. for six days. The chromatogram shows the presence of three peaks at 9, 10.5 and 13 minutes corresponding to the triple-helix conformation, the random coil conformation and mono-saccharides respectively. As discussed above, there is a loss in triple-helix conformation when lentinan is exposed to high temperatures for sustained periods of time. FIG. 2 clearly shows a decrease in the proportion of triple-helix and random coil conformations compared to FIG. 1, indicating that the lentinan has been denatured.

Example 2

The above process was repeated with choline chloride as the ionic liquid extractant for the mushroom granules.

Directly after the extraction with ethyl acetate and ethanol, the mushroom granules were quickly washed with water and filtered. As choline chloride has a melting point of 300° C., it must be used with small amounts of water added to it (in this case, a 2:1 ratio of choline chloride to water is used) to obtain an ionic liquid.

After heating the mushroom granules with this wet choline chloride for 30 minutes, the mixture was filtered through a polypropylene filter and was washed with hot water on the filter 3 times. The liquid extracts were combined and the water was evaporated to give a choline chloride solution of crude lentinan. This was then treated as before in the IMS precipitation stages.

Example 3

300 g of dried Shitake mushrooms were washed with 2 liters of boiling industrial methylated spirits (IMS) and then filtered to recover the IMS.

The resulting precipitate was washed with water and then filtered, with the water phase being disposed.

The resulting precipitate was then washed with approximately 3 to 5 liters of hot water (temperature of from 80° C. to less than 100° C. This wash step was repeated three times. Following washing, the water was removed by means of a rotary evaporator to give a crude lentinan gel.

The gel was dissolved in a mixture of [$C_4$mim]Cl (1-butyl-3-methylimidazolium chloride) (50 g) and water (50 ml), with any remaining solids being filtered off.

The solution was then carefully added to IMS to precipitate out the lentinan, which was then dried and ground to a powder.

A yield of 1.5 g was obtained.

Extraction of Lentinan from Commercial Water Extractions of Shitake Mushrooms.

For low MW lentinan, derived from Chinese freeze dried mushroom extracts, labelled and assayed 50% polysaccharides, the water soluble lentinan polysaccharides contained therein can be isolated in over 90% purity as measured on a gel-HPLC column.

Example 4

The lentinan extract comes as a yellow-brown powder, which is mostly soluble in water.

The powder (5.0 g) was completely dissolved in a liquid mixture of 80 to 90% [$C_4$mim]Cl and 10 to 20% water mixture at room temperature or up to 40° C. Industrial alcohol (97 to 98% ethanol and 2 to 3% methanol mixture) (5 ml) was carefully added to a stirred solution of the crude mushroom extract in [$C_4$mim]Cl.

During the addition, an off-white precipitate formed that was isolated by vacuum filtration using a 30 ml S2 sintered filtered funnel. The precipitate was washed with a 50/50 mixture of industrial alcohol and water, to give an off-white powder on drying (1.7 g).

Figure 3:
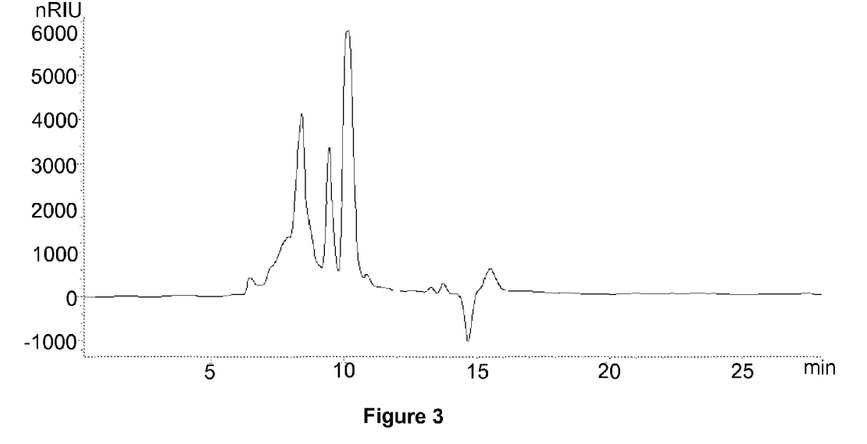
FIG. 3 is a gel-HPLC analysis of the commercial lentinan extracts as supplied.
Figure 4:
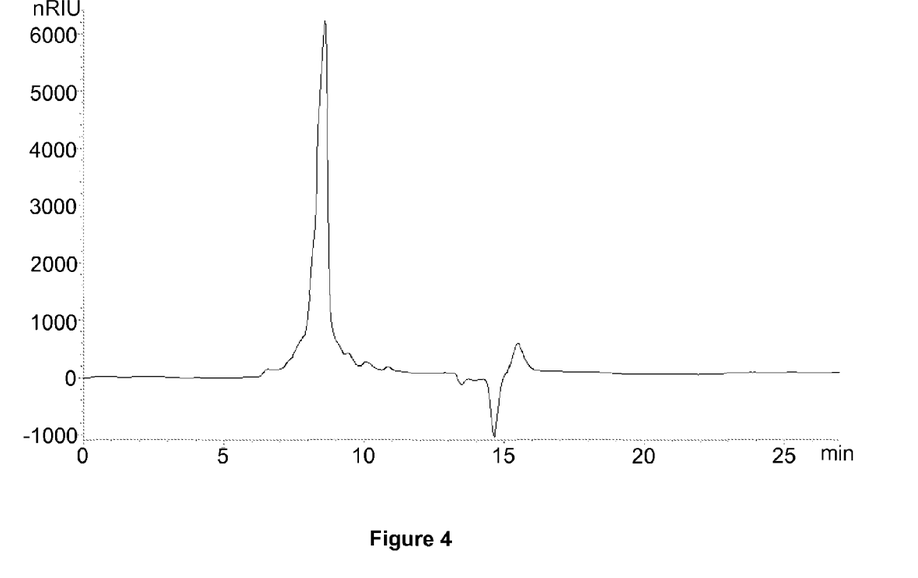
FIG. 4 is a gel-HPLC analysis of commercial lentinan extracts, purified with [C$_4$mim]Cl.

Analysis of the off white powder revealed that its 1H NMR (low resolution in $D_2O$) was consistent with literature spectra, and the gel-HPLC analysis showed that it was a single substance with a retention time of 8 minutes (see FIGS. 3 and 4).

FIG. 3 relates to the untreated extract (Note, the peaks around 15 minutes are an artefact of the HPLC process and are not due to the presence a compound). Three elution peaks can be observed at approximately 8.5, 9.5 and 10.5 minutes corresponding to the triple-helix conformation, the inactive random coil conformation and the presence of mono-saccharides respectively. The chromatogram indicates a large proportion of the extract correspond to the mono-saccharides and other non-polymeric compounds.

FIG. 4 relates to the treated extract with an estimated purity of 90 to 95% lentinan (Note, the peaks around 15 minutes in FIGS. 3 and 4 are believed to be an artefact of the HPLC process and are not due to the presence of a second compound). After purification of the lentinan extract using [$C_4$mim]Cl only one elution peak is observed between 8 and 9 minutes. The results indicate that the ionic liquids are, at least partially, selective towards to the active triple-helix structure.

Example 5

The yellow-brown powder (350 g) was completely dissolved in a liquid mixture of 50-50 [$C_4$mim]Cl and water (700 ml) at 40° C. Industrial alcohol (97 to 98% ethanol and 2 to 3% methanol mixture) (700 ml) was carefully added to a stirred solution of the crude mushroom extract in [$C_4$mim] Cl.

During the addition, a pale brown precipitate formed that was isolated by vacuum filtration using a 1 liter S1 sintered filtered funnel. The precipitate was washed with a 50/50 mixture of industrial alcohol and water, to give an off pale brown powder on drying. The precipitate was dissolved in water (250 ml), and was re-precipitated from water with industrial alcohol (250 ml). This stage gave only marginal improvements in purity and demonstrates that the ionic liquid is essential in the purification process.

Finally, the light brown precipitate was dissolved in [$C_4$mim]Cl/water (80/20), and precipitated with industrial alcohol, to give a white powder.

Figure 5:
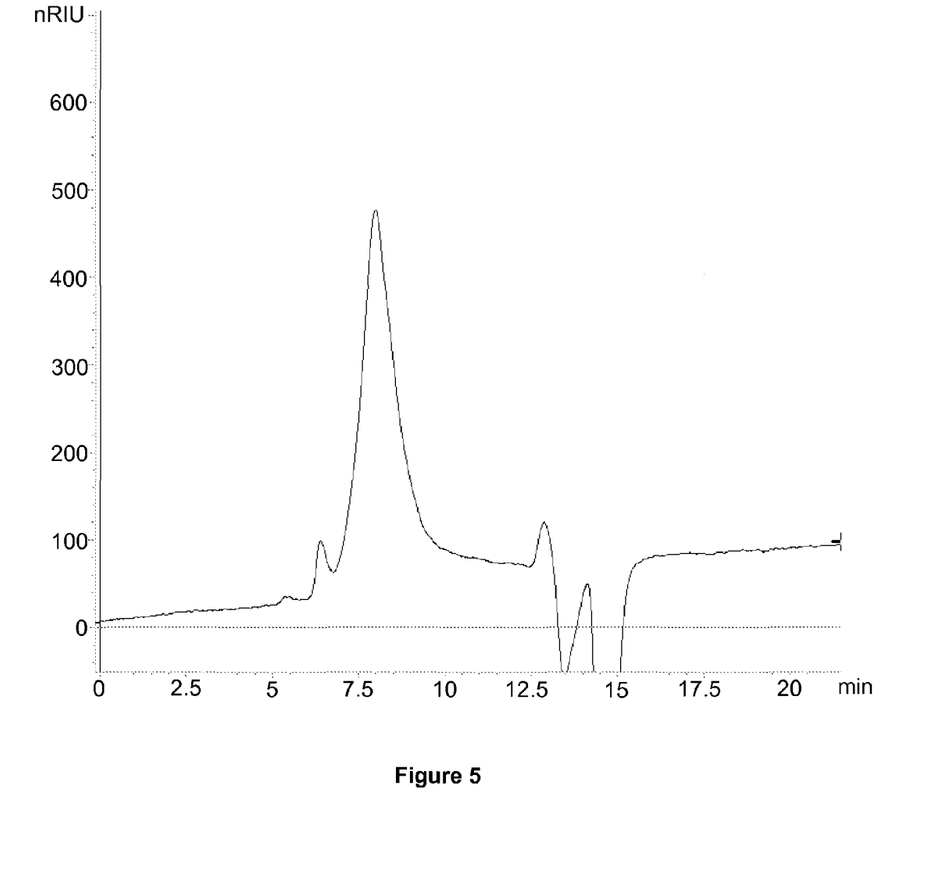
FIG. 5 is a further gel-HPLC analysis of commercial lentinan extracts, purified with [C$_4$mim]Cl.

The analysis of the off white powder revealed that its 1H NMR (low resolution in $D_2O$) was consistent with literature spectra, and the gel-HPLC analysis showed that it was over 95% lentinan, with a retention time of 8 minutes (see FIG. 5). The estimated purity is 90 to 95% lentinan.

For reference, the peaks around 15 minutes shown in FIG. 5 are believed to be an artefact of the HPLC process and are not due to the presence of other compounds. The small peak at 7 minutes is a high molecular weight impurity and accounts for only 4% of the product.

FIG. 5 relates to the purification of commercially available lentinan (FIG. 3), wherein the extraction solution comprises a 50:50 water/[$C_4$mim]Cl solution. The chromatogram only displays one elution peak between 7 and 9.5 minutes. The purification method using a 50:50 water/[$C_4$mim]Cl solution produces a much broader peak than that observed when using a solution mixture of 80 to 90% [$C_4$mim]Cl and 10 to 20% water mixture (FIG. 4). The broader resonance corresponds to an increase in the range of molecular weight of the lentinan extracted.

Purification of Lentinan Extracts Using Counter-Current Chromatography (CCC)

The Chinese freeze dried mushroom extracts (yellow-brown powder) were further purified using counter-current chromatography (CCC).

Figure 6:
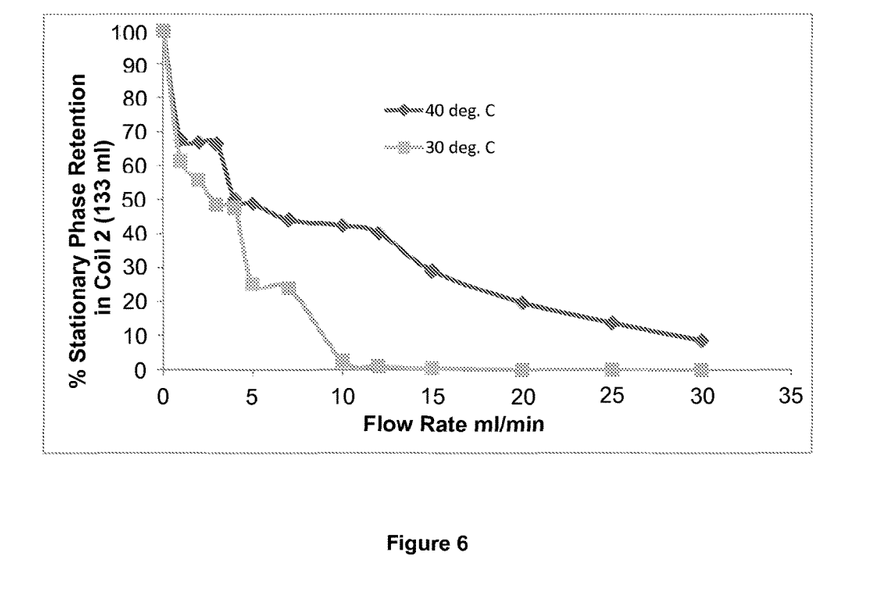
FIG. 6 is a stationary phase retention curve for a CCC solvent system at 30° C. and 40° C.

In order to determine the required flow rate, the retention time of the stationary was first assessed (see FIG. 6).

A dipotassium phosphate solution in water (250 ml) was mixed with [$C_4$mim]Cl (250 ml) and industrial methylated spirits (50 ml). Degassing of the solution was achieved using sonification, after which two phases were formed, an aqueous phase (stationary phase) and a less dense ionic liquid phase (mobile phase).

The retention experiments were performed using an IL-prep CCC, based on a J-type centrifuge containing a 133 ml, 2.1 diameter coil of 36 meters in length. Both phases were pumped into the column wherein the pump for the stationary phase was located at the bottom of the reservoir and the pump for the mobile phase located at the top of the reservoir. The experiments were performed using a rotation speed of 865 rpm and at temperatures of 30° C. and 40° C.

FIG. 6 illustrates the dependency of stationary phase retention on the flow rate of the mobile phase. FIG. 6 indicates that the highest level of retention is achieved at conditions of 1 to 2 ml/min at 40° C., 865 rpm.

Example 6

The mobile phase was pumped into a CCC column, containing only stationary phase, at a low rate of 2.5 ml/min. Once phase retention became constant at 67%, the flow rate of the mobile phase was reduced to 1.0 ml/min.

Commercial lentinan (1.5 g) was dissolved in a mixture of ionic liquid mobile phase (2.5 ml) and aqueous stationary phase (5 ml). Once dissolved, the solution was loaded on to the 5.0 ml injection loop and subsequently injected onto the 133 ml coil at a flow rate of 1.0 ml/min.

A total of 40 fractions were collected, each fraction containing 5 ml of mobile phase. Fractions 23 to 35 were combined and ethanol was added to the solution in order to precipitate lentinan. The precipitate was subsequently filtered, washed using ethanol, and dried to produce a slightly off-white powder (0.45 g).

It was noted that a small amount of stationary phase bleeding occurred preceding the elution of lentinan.

The invention claimed is:

1. A method of extracting lentinan from lentinan containing mushrooms comprising a step of contacting the mushrooms with an ionic liquid in order to obtain a lentinan rich ionic liquid solution and wherein the contact time is between 10 minutes and 48 hours and the contacting takes place at a temperature of 15 to 90° C., further comprising a step of pre-treating the lentinan containing mushrooms at a temperature of less than 100° C.

2. The method of claim 1, wherein the ionic liquid is hydrophilic.

3. The method of claim 2, wherein the ionic liquid has at least one member of a group consisting of a hydrophilic cation and a hydrophilic anion.

4. A method of claim 3, wherein the cation is selected from ammonium, azaannulenium, azathiazolium, benzofuranium, borolium, diazabicyclodecenium, diazabicyclononenium, diazabicycloundecenium, dithiazolium, furanium, imidazolium, indolinium, indolium, morpholinium, oxaborolium, oxaphospholium, oxazinium, oxazolium, iso-oxazolium, oxothiazolium, pentazolium, phospholium, phosphonium phthalazinium, piperaziniumpiperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenozolium, tetrazolium, iso-thiadiazolium, thiazinium, thiazolium, thiophenium, triazadecenium, triazolium and iso-triazolium.

5. The method of claim 3, wherein the cation is selected from:

wherein: $R^a$, $R^b$, $R^c$, $R^d$, $R^e$, $R^f$ and $R^g$ are each independently selected from hydrogen, a $C_1$ to $C_{10}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —$(CH_2)_q$— wherein q is from 3 to 6; and wherein said alkyl, cycloalkyl or aryl groups or said methylene chain are unsubstituted or may be substituted by one to three groups selected from: $C_1$ to $C_6$ alkoxy, $C_3$ to $C_8$ cycloalkyl, $C_6$ to $C_{10}$ aryl, $C_7$ to $C_{10}$ alkaryl, $C_7$ to $C_{10}$ aralkyl, —O, —OH, —NO$_2$, —CO$_2R^x$, —OC(O)$R^x$, —C(O)$R^x$, —NR$^x$C(O)NR$^y$R$^z$, —NR$^x$C(O)OR$^y$, —OC(O)NR$^y$R$^z$, —C(O)NR$^y$R$^z$, —NR$^y$R$^z$, or a heterocyclic group, wherein $R^x$, $R^y$ and $R^z$ are independently selected from hydrogen or $C_1$ to $C_6$ alkyl.

6. The method of claim 5, wherein $R^a$, $R^b$, $R^c$, $R^d$, $R^e$, $R^f$ and $R^g$ are each independently selected from hydrogen, a $C_1$ to $C_{10}$, straight chain or branched alkyl.

7. The method of claim 5, wherein $R^a$ and $R^g$ are each independently selected from $C_1$ to $C_8$, linear or branched, alkyl.

8. The method of claim 5, wherein $R^a$ and $R^g$ are each independently selected from methyl, ethyl, n-propyl, n-butyl, n-pentyl, n-hexyl, n-heptyl and n-octyl.

9. The method of claim 5, wherein $R^b$, $R^c$, $R^d$, $R^e$ and $R^f$, are each hydrogen or are each independently selected from $C_1$ to $C_8$, linear or branched, alkyl.

10. The method of claim 5, wherein $R^b$, $R^c$, $R^d$, $R^e$ and $R^f$ are each hydrogen or are each independently selected from methyl, ethyl, n-propyl, n-butyl, n-pentyl, n-hexyl, n-heptyl and n-octyl.

11. The method of claim 5, wherein $R^b$, $R^c$, $R^d$, $R^e$ and $R^f$ are each hydrogen.

12. The method of claim 5, wherein the cation is selected from:

wherein: $R^a$, $R^b$, $R^c$, $R^d$, $R^e$, $R^f$, and $R^g$ are defined in claim 5.

13. The method of claim 12, wherein the cation is selected from:

wherein: $R^a$ and $R^g$ are as defined in claim 5, and $R^h$ represents hydrogen or a methyl group.

14. The method of claim 5, wherein the cation is selected from:

15. A method of claim 3, wherein the cation is selected from:

$[N(R^a)(R^b)(R^c)(R^d)]^+$ wherein: $R^a$, $R^b$, $R^c$ and $R^d$ are each independently selected from hydrogen, a $C_1$ to $C_{10}$, straight chain or branched alkyl group, a $C_3$ to $C_8$ cycloalkyl group, or a $C_6$ to $C_{10}$ aryl group; and wherein said alkyl, cycloalkyl or aryl groups or said methylene chain are unsubstituted or may be substituted by one to three groups selected one to three groups selected from: $C_1$ to $C_6$ alkoxy, $C_3$ to $C_8$ cycloalkyl, $C_6$ to $C_{10}$ aryl, $C_7$ to $C_{10}$ alkaryl, $C_7$ to $C_{10}$ aralkyl, —O, —OH, —NO$_2$, —CO$_2R^x$, —OC(O)$R^x$, —C(O)$R^x$, —NR$^x$C(O)NR$^y$R$^z$, —NR$^x$C(O)OR$^y$, —OC(O)NR$^y$R$^z$, —C(O)NR$^y$R$^z$, —NR$^y$R$^z$, or a heterocyclic group, wherein $R^x$, $R^y$ and $R^z$ are independently selected from hydrogen or $C_1$ to $C_6$ alkyl, and wherein one of $R^a$, $R^b$, $R^c$ and $R^d$ may also be hydrogen.

16. The method of claim 15, wherein $R^a$, $R^b$, $R^c$ and $R^d$ are each independently selected from hydrogen, a $C_1$ to $C_{10}$, straight chain or branched alkyl.

17. The method of claim 15, wherein one of $R^a$, $R^b$, $R^c$ and $R^d$ is hydrogen.

18. The method of claim 15, wherein $R^a$, $R^b$, $R^c$ and $R^d$ are independently selected from methyl, ethyl, n-propyl, n-butyl, n-pentyl, n-hexyl, n-heptyl, and n-octyl.

19. The method of claim 15, wherein two or more of $R^a$, $R^b$, $R^c$ and $R^d$ are independently selected from methyl, ethyl, propyl and butyl.

20. The method of claim 15, wherein three or more of $R^a$, $R^b$, $R^c$ and $R^d$ are independently selected from methyl, ethyl, propyl and butyl.

21. The method of claim 15, wherein $R^b$, $R^c$, and $R^d$ are each the same alkyl group selected from methyl, ethyl n-butyl, and n-octyl, and $R^a$ is selected from hydrogen, methyl, n-butyl, n-propyl, n-pentyl, n-hexyl, n-hepty n-octyl, n-tetradecyl, 2-hydroxyethyl, or 4-hydroxy-n-butyl.

22. The method of claim 15, wherein the cation is selected from:

23. The method of claim 1, wherein the anion is selected from inorganic anions, sulfonate anions, fluorinated anions, sulphate anions, carboxylate anions, carbonate anions and metal anions.

24. The method of claim 23, wherein the anion is selected from [F]$^-$, [Cl]$^-$, [Br]$^-$, [CH$_3$CO$_2$]$^-$ and [CH$_3$CH$_2$CO$_2$]$^-$.

25. The method of claim 23, wherein the inorganic anions are selected from [F]$^-$, [Cl]$^-$, [Br]$^-$, [I]$^-$, [NO$_3$]$^-$, [BF$_4$], [HSO$_4$]$^-$, and [SO$_4$]$^{2-}$; the fluorinated anions are selected from [CF$_3$CO$_2$]$^-$, [CF$_3$SO$_3$]$^-$ and [(C$_2$F$_5$)$_3$PF$_3$]$^-$; the sulfonate anions are selected from [CH$_3$SO$_3$]$^-$, [C$_2$H$_5$SO$_3$]$^-$ and [bis(2-ethylhexyl)-sulfosuccinate]$^-$ (also referred to as [AOT]$^-$); the carboxylate anions are selected from [CH$_3$CO$_2$]$^-$ and [CH$_3$CH$_2$CO$_2$]$^-$; the carbonate anion is [HCO$_3$]$^-$; or the sulphate anions are selected from [CH$_3$OSO$_3$]$^-$, [C$_2$H$_5$OSO$_3$]$^-$, [C$_8$H$_{17}$OSO$_3$]$^-$, and [H$_3$C(OCH$_2$CH$_2$)$_n$OSO$_3$]$^-$.

26. The method of claim 1, wherein the ionic liquid further comprises water, acetate, lactates, dicyanamides, aqueous phosphates or urea.

27. The method of claim 26, wherein the ionic liquid includes water, and wherein the non-water ionic liquid component to water ratio is from 99:1 to 50:50.

28. The method of claim 26, wherein the ionic liquid includes water, and wherein the non-water ionic liquid component to water ratio is from 99:1 to 75:25.

29. The method of claim 1, wherein the contacting takes place at a temperature of 15 to 80° C.

30. The method of claim 1, wherein the contacting takes place at a temperature of 60 to 80° C.

31. The method of claim 1, wherein the contact time is from 30 minutes to 4 hours.

32. The method of claim 1, wherein the lentinan containing mushrooms are in wet form are masticated prior to contacting with the ionic liquid.

33. The method of claim 1, further comprising a step of drying the lentinan rich ionic liquid solution.

34. The method of claim 1, further having a step from at least one member of a group consisting of: filtering the lentinan rich ionic liquid solution to remove mushroom matter; precipitating the lentinan from the lentinan rich ionic liquid solution; washing the precipitated lentinan; drying the precipitated lentinan; freeze drying the precipitated lentinan; spray drying the precipitated lentinan; purifying the lentinan using counter-current chromatography; and subjecting extracted lentinan to a dialysis process.

35. The method of claim 34, wherein an alcohol is used for any precipitation.

36. The method of claim 35, wherein the alcohol is selected from methanol, ethanol, iso-propanol and combinations thereof.

37. The method of claim 34, wherein an ionic liquid based counter-current chromatography solvent system is used for any counter-current chromatography.

38. The method of claim 1, wherein the pre-treatment step comprises a wax removal step.

39. The method of claim 1, wherein the pre-treatment step comprises a steroid removal step.

40. The method of claim 1, wherein the lentinan containing mushrooms have not been dried prior to contacting with the ionic liquid.

41. The method of claim 1, wherein the pre-treatment step comprises a sugar removal step.

42. A method of extracting lentinan from lentinan containing mushrooms comprising a step of contacting the mushrooms with an ionic liquid in order to obtain a lentinan rich ionic liquid solution and wherein the contacting takes place at a temperature of 15 to 90° C., further comprising a step of pre-treating the lentinan containing mushrooms at a temperature of less than 100° C., and wherein the pre-treatment step comprises a wax removal step.

43. A method of extracting lentinan from lentinan containing mushrooms comprising a step of contacting the mushrooms with an ionic liquid in order to obtain a lentinan rich ionic liquid solution and wherein the contacting takes place at a temperature of 15 to 90° C., further comprising a step of pre-treating the lentinan containing mushrooms at a temperature of less than 100° C., and wherein the pre-treatment step comprises a steroid removal step.

* * * * *